US011802836B2

(12) United States Patent
Vlandas et al.

(10) Patent No.: US 11,802,836 B2
(45) Date of Patent: *Oct. 31, 2023

(54) OPTICAL DETECTION METHOD

(71) Applicants: Universite De Lille, Lille (FR); Centre National De La Recherche Scientifique, Paris (FR)

(72) Inventors: Alexis Vlandas, Villeneuve d'Ascq (FR); Julien Wengler, Paris (FR); Sebastien Lamant, Lille (FR); Vincent Senez, Baisieux (FR)

(73) Assignees: Universite De Lille, Lille (FR); Centre National De La Recherche Scientifique, Paris (FR)

( * ) Notice: Subject to any disclaimer, the term of this patent is extended or adjusted under 35 U.S.C. 154(b) by 819 days.

This patent is subject to a terminal disclaimer.

(21) Appl. No.: 16/618,639

(22) PCT Filed: Jun. 1, 2018

(86) PCT No.: PCT/EP2018/064499
§ 371 (c)(1),
(2) Date: Dec. 2, 2019

(87) PCT Pub. No.: WO2018/220191
PCT Pub. Date: Dec. 6, 2018

(65) Prior Publication Data
US 2021/0148815 A1 May 20, 2021

(30) Foreign Application Priority Data
Jun. 2, 2017 (FR) ...................... 1754930

(51) Int. Cl.
*G01N 21/41* (2006.01)
*G01N 21/47* (2006.01)
*G01N 21/45* (2006.01)
*C12Q 1/34* (2006.01)
*G01N 21/55* (2014.01)
*G01N 21/77* (2006.01)

(52) U.S. Cl.
CPC ........... *G01N 21/4133* (2013.01); *C12Q 1/34* (2013.01); *G01N 21/55* (2013.01); *G01N 21/77* (2013.01)

(58) Field of Classification Search
CPC .... G01N 21/4133; G01N 21/35; G01N 21/77; G01N 21/41; G01N 21/4788; G01N 21/55; C12Q 1/34
See application file for complete search history.

(56) References Cited

U.S. PATENT DOCUMENTS

| 5,468,606 A | 11/1995 | Bogart et al. |
| 2003/0190612 A1 | 10/2003 | Yamamoto et al. |
| 2006/0134601 A1 | 6/2006 | Torres et al. |
| 2006/0226008 A1 | 10/2006 | Rodgers et al. |
| 2013/0115643 A1* | 5/2013 | Cathala et al. .......... C12Q 1/34 435/18 |
| 2017/0038380 A1* | 2/2017 | Tao et al. ............. G01N 33/557 |

FOREIGN PATENT DOCUMENTS

| FR | 2962545 A1 | 1/2012 |
| JP | 2002-065274 A | 3/2002 |
| JP | 2002-509274 A | 3/2002 |
| JP | 2002-122601 A | 4/2002 |
| JP | 2003-528311 A | 9/2003 |
| JP | 2010-509593 A | 3/2010 |
| JP | 2010265450 A | 11/2010 |
| KR | 20090024965 A | 3/2009 |
| WO | 94/03774 A1 | 2/1994 |
| WO | 99/36760 A1 | 7/1999 |
| WO | 01/71322 A2 | 9/2001 |
| WO | 2003062334 A1 | 7/2003 |
| WO | 2008/127402 A2 | 10/2008 |
| WO | 2012004536 A1 | 1/2012 |
| WO | 2017066213 A1 | 4/2017 |

OTHER PUBLICATIONS

Preetam Anbukarasu et al. "A diffraction-based degradation sensor for polymer thin films", Polymer Degradation and Stability, vol. 142, pl. 102-110, (2017).
English translation of Japanese Office Action for JP Pat. App. No. 2019-566573 dated Mar. 10, 2022 (15 pages).
Non-Final Office Action issued in U.S. Appl. No. 16/618,605 dated Jul. 19, 2022 (10 pages).
Japanese Office Action ("JP OA") for JP App. No. 2020-516958 dated Apr. 25, 2022 (3 pages).
Notice of Allowance issued for U.S. Appl. No. 16/618,605 dated Dec. 15, 2022 (9 pages).
International Search Report (ISR) for PCT/EP2018/064499 dated Jun. 29, 2018 (7 pages).
Corinna Schuler et al. "Decomposable Hollow Biopolymer-Based Capsules", Biomacromolecules, vol. 2, No. 3, p. 921-926, (Nov. 3, 2001).
Hong Wu et al. "Molecularly imprinted organic-inorganic hybrid membranes for selective separation of phenylalanine isomers and its analogue", Separation and Purification Technology, vol. 68, p. 97-104 (2009).

(Continued)

*Primary Examiner* — Satyendra K Singh
(74) *Attorney, Agent, or Firm* — Shumaker, Loop & Kendrick, LLP

(57) ABSTRACT

A process for detecting the sensitivity of one or more polymers and/or of one or more, mixtures of polymers to a compound, including the steps of exposing at least one lens-shaped micro-deposit, including the polymer(s) and/or the mixture(s) of polymers, to the compound, and detecting, by illuminating the surface of this micro-deposit, a change in the spatial distribution of the intensity of the light reflected or transmitted by this micro-deposit, linked to a variation in the dimensions and/or refractive index of this micro-deposit, under the effect of an interaction between the polymer(s) and/or the mixture(s) of polymers and the compound.

31 Claims, 3 Drawing Sheets

(56) References Cited

OTHER PUBLICATIONS

Vincent Ducere et al. "A capacitive humidity sensor using cross-linked cellulose acetate butyrate", Sensors and Actuators B, vol. 106, p. 331-334 (2005).

Huiyan Li et al. "Hydrogel droplet microarrays with trapped antibody-functionalized beads for multiplexed protein analysis", Lab Chip, vol. 11, p. 528-534 (2011).

Shouichi Sakakihara et al. "A single-molecule enzymatic assay in a directly accessible femtoliter droplet array", Lab Chip, vol. 10, p. 3355-3362 (2010).

Jens Voskuhl et al. "Advances in contact printing technologies of carbohydrate, peptide, and protein arrays", Current Opinion in Chemical Biology. vol. 18, p. 1-7 (2014).

Nobutoshi Komuro et al. "Inkjet printed (bio)chemical sensing devices", Anal Bioanal Chem, vol. 405, p. 5785-5805 (2013).

Archana N. Rao et al. "Biophysical properties of nucleic adds at surfaces relevant to microarray performance", Biomater. Sci., vol. 2, p. 436-471 (2014).

Christiane L. Salgado et al., "Combinatorial cell-3D biomaterials cytocompatibility screening for tissue engineering using bioinspired superhydrophobic substrates", Integr. Biol., vol. 4, p. 318-327 (2012).

* cited by examiner

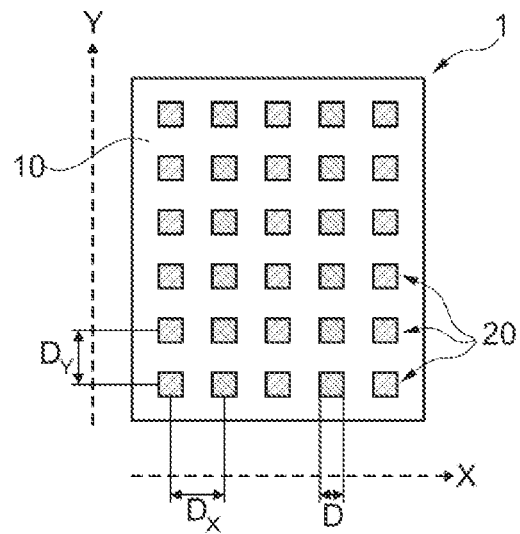
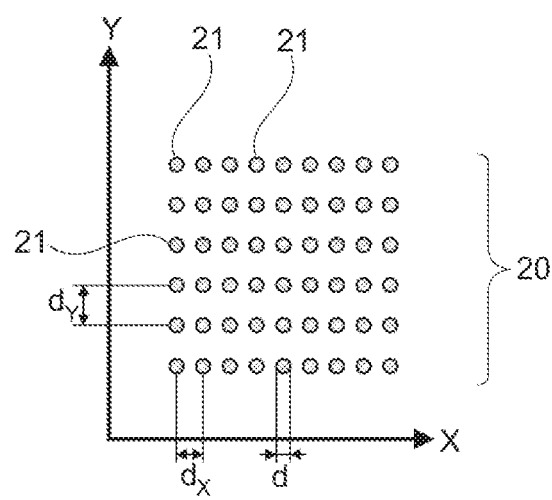
Fig. 1　　　　Fig. 2
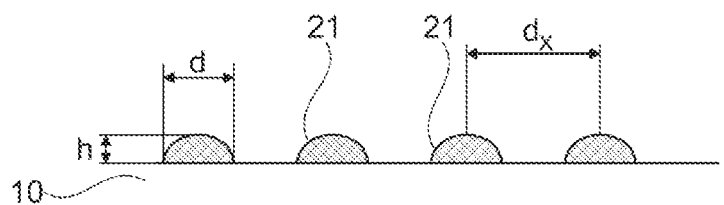
Fig. 3

OPTICAL DETECTION METHOD

TECHNICAL FIELD AND BACKGROUND

The present invention relates to the detection of the sensitivity of one or more polymers to a compound, in particular that of one or more biopolymers to an enzyme.

In the rest of the document, according to the invention the term "polymer" refers to a natural or synthetic homopolymeric or heteropolymeric polymer, the structure of which may be crystalline, amorphous or hybrid (amorphous and crystalline), or a mixture of "polymers" defined as above.

The polymer according to the invention (single or mixture) may be supplemented with a chemical agent creating covalent bonds between the chains of the polymer (or of the polymer mixture). This chemical agent may be a thermosetting resin, depending on the chains to be bonded. The term "resin" refers to a chemical substance which has the capacity of forming covalent bonds with the "polymer" via an energy input of thermal, photonic or chemical type.

The term "compound" refers to a chemical or biological agent which has the capacity of chemically or physically modifying the refractive index and/or the geometry of the "polymer" deposit. In many technical and industrial fields, the identification and study of enzymes with degrading activity on natural or synthetic polymers is a major challenge.

For example, certain degradation enzymes, for example hydrolytic enzymes, are an essential tool for generating biofuels from lignocellulose-rich biomass.

More precisely, plant walls are complex structures formed from entangled polymers (cellulose, hemicelluloses, lignins, pectins, etc.); degradation enzymes are used, for example, to break cellulose and hemicellulose chains into sugars intended to be fermented in order to create bioethanol, among other applications.

To this end, it is advantageous to use technical devices which allow the rapid, simple and reliable detection of the degradation activity of an enzyme, or of a combination of enzymes, toward a polymer or a combination of polymers.

It is in particular common practice to use dedicated colorimetric devices, which use chemical reactions to reveal the enzymatic activity. These colorimetric devices use for this purpose chemical detection dyes or indicators.

The majority of the existing enzymatic tests make it possible to study an enzyme or a type of microorganism which expresses an enzyme in the multiwell plate format, to the wells of which is added a substrate (for example a polymer), which, under the action of the enzyme, is converted into a fluorescent or colored product. This format requires the production of modified substrates (addition of a fluorescent molecule or of a colored chemical compound). It is also possible to reveal the presence of a reaction product by adding a chromogenic reagent. In these two cases, the volumes of material are at the minimum a few microliters. It requires advanced and expensive automated tools, and extremely sensitive photon sensors.

Colorimetric devices for detecting hydrolytic activity toward one or more polymers are thus often complex to use and require many manipulations and reagents. When no chromogenic substrate or reagent is used, it is necessary to employ analytical tools such as mass spectrometry, chromatography, infrared spectrometry or nuclear magnetic resonance. Despite the numerous advantages of these tools (sensitivity, specificity of detection of the catalytic act), they require expensive equipment and particular expertise for their use.

Other devices use interferometry to detect the degradation activity of a polymer.

These devices include for this purpose at least one transparent thin film of polymer applied on a reflective support (conventionally silicon). The thickness of this transparent film is within a range of values allowing the appearance of a particular color due to an optical interference phenomenon, resulting from the fact that a portion of the incident beam is reflected at the air/film interface, whereas another portion of the incident beam is refracted and then reflected at the film/support interface. The interference of the reflected beams and of the refracted beams creates an interference pattern. The resulting color corresponds to the wavelength at which the constructive interference is maximal.

A device of this type is described in patent application FR 2 962 545, being intended in particular for detecting the hydrolytic activity toward a polymer, typically a polysaccharide, mainly constituting the material of the thin transparent film deposited on the reflective support.

The studies conducted have shown that, for an incubation time of a few tens of minutes, this method has a sensitivity threshold that is from 125 to 1000 times lower than the methods conventionally used in enzyme identification.

This method however has certain limitations.

Specifically, it causes substantial loss of material during the manufacture of the thin film since a large portion of the surface of the support must be coated with polymer, and continuously coated, to allow light interferences to be manifested. By using the centrifugal coating technology, the loss of material is considerable (more than 90%), which is a major drawback in terms of industrialization, or when the polymer to be tested is only available in very small amount.

The spreading of a single polymer or of a single mixture of polymers per support also represents a limit of this method.

SUMMARY

There is thus a need for a new process for detecting enzymatic activity which overcomes all or some of the above drawbacks, and in particular which does not require a large amount of polymer, and/or which makes it easily possible to test several polymers and/or several enzymes with the same device.

The invention is also directed toward providing, if so desired, a process for precisely and quantitatively measuring the hydrolysis of a polymer by an enzyme, for example by monitoring the hydrolysis kinetics.

BRIEF DESCRIPTION OF THE FIGURES

The invention may be understood more clearly on reading, the detailed description attached drawing, in which:

FIG. 1 represents in top view an example of a device according to the invention, FIG. 2 represents schematically in enlarged scale a macropattern, FIG. 3 represents in cross section micro-deposits.

FIG. 9 illustrates the effect of the enzymatic solution on the, micro-deposits.

DETAILED DESCRIPTION

Detection Process

Figure 4:
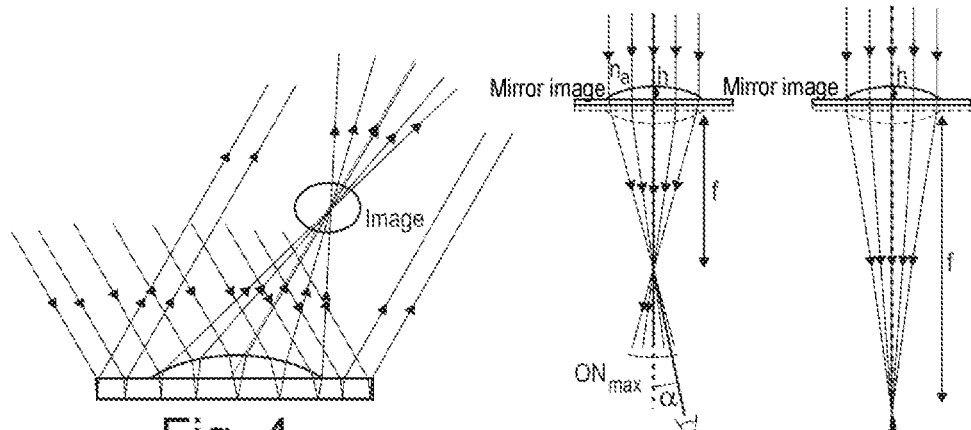
FIG. 4 illustrates the observation of a micro-deposit in reflection, before degradation.

According to a first subject, the present invention relates to a process for detecting the sensitivity of a polymer or of a mixture of polymers to a compound, including the steps consisting in:
  exposing at least one micro-deposit, which is preferably lens-shaped, including the polymer or the mixture of polymers, to the compound,
  detecting a change in the spatial distribution of the intensity of the light reflected or transmitted by this micro-deposit, linked to a variation in the dimensions and/or refractive index of this micro-deposit, under the effect of an interaction between the polymer or the mixture of polymers and the compound.

The present invention also relates to a process for detecting the sensitivity of one or more polymers and/or of one or more mixtures of polymers to a compound, including the steps consisting in:
  exposing at least one lens-shaped micro-deposit, including the polymer(s) and/or the mixture(s) of polymers, to the compound,
  detecting, by illuminating the surface of this micro-deposit, a change in the spatial distribution of the intensity of the light reflected or transmitted by this micro-deposit, linked to a variation in the dimensions and/or refractive index of this micro-deposit, under the effect of an interaction between the polymer(s) and/or the mixture(s) of polymers and the compound.

The micro-deposits according to the invention may be monolayers, i.e. including a single layer, and/or may be multilayers, i.e. including several superposed layers.

Each layer may include the polymer or the mixture of polymers.

In the case where the micro-deposit is a monolayer, this monolayer may be in the form of a single block including the polymer or the mixture of polymers. The monolayer is placed on a support, preferably in contact with said support. Preferably, this monolayer is lens-shaped.

In the case where the micro-deposit is a multilayer, this multilayer may have two layers, notably with a core-shell architecture. The micro-deposit may then have a first layer corresponding to a core, and a second layer corresponding to a shell.

The first layer may be placed on the support, preferably in contact therewith, and may be lens-shaped.

The second layer may at least partially and preferably totally cover the first layer and may have a form complementary to that of the first layer.

The first and second layers may each have a face facing the support, referred to as the inner face, and a face opposite the face that is facing the support, known as the outer face.

Preferably, the inner face of the first layer is in contact with the support.

Preferably, the outer face of the first layer is convex and is in contact with the inner face of the second layer.

The micro-deposit including two layers with a core-shell architecture may have a core comprising, for example, only one first polymer and a shell comprising, for example, only one second polymer different from the first one, or a core comprising several polymers and a shell comprising several polymers, or a core comprising only one polymer and a shell comprising several polymers, or alternatively a core comprising several polymers and a shell comprising only one polymer. The type of micro-deposit chosen is suited to the intended application.

The step of exposing the micro-deposit(s) to the compound may comprise a period of incubation at room temperature, which may last, for example, from 1 to 240 minutes. This step may be followed by a washing step and a drying step.

When the interaction between the polymer(s) and the compound is a degradation of the polymer(s) by the compound, the micro-deposit containing the polymer(s) will decrease in volume. If the polymer(s) are not sensitive to the compound with which they are placed in contact, the micro-deposit containing the polymer(s) will maintain its volume and its shape.

Preferably, when the interaction between the polymer and the compound is a degradation of the polymer by the compound, the micro-deposit containing the polymer will decrease in volume. If the polymer is not sensitive to the compound with which it is placed in contact, the micro-deposit containing the polymer will maintain its volume and its shape.

The decrease in volume of the micro-deposits brings about, at the macroscopic scale, a difference in appearance relative to the micro-deposits which conserve their volume. This difference in contrast may be observable with the naked eye.

Thus, according to one example of implementation of the invention, a comparison of the appearance of an assembly of micro-deposits exposed to the compound and of an assembly of micro-deposits not exposed to the compound is performed, in order to detect a change in appearance. This comparison may be performed without magnification, in reflected light.

According to one embodiment, the observation of the appearance of the contrast is performed using one or more suitable measuring instruments, notably using a camera and preferably an image processing program. This program may notably automatically detect a variation in appearance and the appearance of a contrast, or even may quantify it.

The invention also makes it possible to measure the degradation of the micro-deposits by measuring the alteration of the far-field optical response of the micro-deposits. This method offers very good sensitivity due to the micrometric size of the deposits and allows quantitative reading that is easy and inexpensive to perform, by means of simple observation using a camera or any other intensity sensor.

In such a process according to the invention, several micro-deposits may be exposed to the compound and detection of the change in the spatial distribution of the light intensity is performed by observation of these micro-deposits.

Detection of the change in the spatial distribution may notably be observed with or without magnification.

The micro-deposit(s) may be illuminated with a point or linear source, better still a linear source.

Observation of the spatial distribution of the light intensity may be performed in the region of the specular reflection, notably in a range 0°-2.5° from the specular reflection.

Observation of the change in spatial distribution may be performed with a matrix sensor.

The micro-deposits may be placed in any type of periodic or non-periodic arrangement. The micro-deposits may notably be placed in the form of a network or matrix.

According to one embodiment, the micro-deposits are placed in a periodic network and illuminated with a coherent light, notably of LASER type. Observation of the spatial distribution of the light in a diffraction pattern produced by the network makes it possible to measure the degradation of the micro-deposits.

Information regarding the variation in the volume of the micro-deposit can be generated from the observed change, by comparison with reference data, these data possibly being experimental or obtained by modeling from the form of the deposits.

The compound may be an enzyme, the interaction between the compound and the polymer(s), preferably between the compound and the polymer, preferably being a degradation of the polymer(s), preferably of the polymer, by the compound.

The above interaction may be accompanied by a variation in an interference pattern for each micro-deposit.

The variation in the interference pattern offers, when it exists, a means for finer measurement of the interaction.

Detection of a variation of an interference pattern, when it exists, may be performed by interferometry. Preferably, this detection by interferometry is performed after magnification of the interference pattern observed on each micro-deposit. Detection by interferometry may be advantageously accompanied by the reconstruction of the volume of the micro-deposit from the localization of the interference fringes.

The thickness of the micro-deposits is preferably between 100 nm and 5000 nm, better still between 100 and 1500 nm, the thickness of each micro-deposit advantageously passing through only one maximum.

Thus, according to one embodiment, each micro-deposit has a convex outer surface.

The largest dimension of the micro-deposits is preferably between 10 μm and 100 μm.

Preferably, the micro-deposits have a substantially circular contour.

The micrometric-scale micro-deposits are preferably deposited so as to form macro-patterns that are discernible from each other by the naked eye, of millimetric scale. These macro-patterns are preferably separated and detached from each other.

The macro-patterns may be arranged like the wells of a multi-well grid for automated deposition, for example a 96-well grid.

This can facilitate the use of automatic tools for depositing one or more test compounds onto the macro-patterns and then the analysis of any variations in appearance on each macro-pattern, analogously to the observation of a reaction in each well.

According to a preferred embodiment, the micro-deposits are arranged in the form of raster dots (classic or stochastic), the spacing between the raster dots preferably being small enough for the coating formed by the micro-deposits to appear, in a macro-pattern, which is continuous to the naked eye at a distance of 25 cm. The raster may be regular, as may the size of the micro-deposits. In other words, each micro-deposit may not be discernible to the naked eye, whereas the macro-patterns are.

Many techniques exist for producing such an arrangement of micro-deposits: photolithography (Rao, et al., 2014), microcontact (Voskuhl, et al., 2014) and inkjet printing (Komuro, et al., 2013).

According to a preferred embodiment, the micro-deposits are obtained by inkjet printing.

The advantages of inkjet printing are the low value of the volumes ejected (of the order of a picoliter, modulable according to the properties of the liquid or the ejection parameters, allowing a high density of micro-deposits), the absence of contact with the solid support (eliminates any damage of the support and/or of the printing head), the existence of an ink reservoir external to the printing head, which makes it possible to produce several thousand macro-patterns of micro-deposits before depletion of the ink, which greatly improves the reproducibility of the deposits, and a high printing rate, for example up to 500 droplets per second.

The support on which the micro-deposits are located may be solid or flexible, and flat or not flat.

The support is preferably nonporous and smooth.

As a variant, the support is nanostructured to aid control of the wettability.

According to one embodiment, the support consists of an opaque or transparent material having an upper surface with reflective properties.

The term "reflective" means herein total or partial optical reflection, of specular type. The reflection preferably relates to the wavelength range of the visible region.

The support advantageously consists of a silicon wafer.

Preferably, the micro-deposits are located on a hydrophobic support. The hydrophobicity of the support reduces the risk of coalescence of droplets during printing, and facilitates the production of a shape that is convex toward the exterior.

The support may be made hydrophobic via any technique known to those skilled in the art.

A treatment with perfluoro compounds, such as compounds bearing perfluorocarbon groups, may be performed. Mention may be made, for example, of treatment with the gas $C_4F_8$.

As a variant, treatment with perfluorodecyltrichlorosilane (FDTS) is performed.

In another variant, a wet-route treatment is performed, for example by immersing the support for a time of 2 to 18 hours in a solution prepared according to the specificities below, followed by drying:

| | |
|---|---|
| Hexane | 14 mL |
| Dichloromethane | 6 mL |
| Acetic acid | 0.1 mL |
| 3-Methacryloxypropyltrimethoxysilane | 0.1 mL |

The support may have a hydrophobic coating 100 nm thick or less, on which the micro-deposits are produced.

The compound for which interaction with the polymer(s) and/or the mixture(s) of polymers, preferably with the polymer or the mixture of polymers, is studied is typically an enzyme or a set of enzymes, the interaction between the compound and the polymer(s), preferably between the compound and the polymer, preferably being an enzymatic degradation, notably enzymatic hydrolysis of the polymer(s), preferably of the polymer, by the compound.

The polymer(s) may be degradable with an enzyme or a set of enzymes.

As enzymes that are particularly suitable, mention may be made of enzymes of hydrolase type.

During the step of exposing the micro-deposits to the compound, said compound is preferably in solution, notably in aqueous solution.

When it is an enzyme, said enzyme is typically in aqueous solution, under conditions that are suitable for enzymatic hydrolysis.

The term "enzymatic hydrolysis" denotes a mechanism performed by an enzyme of hydrolase type, catalyzing a biochemical hydrolysis reaction.

Among the enzymes of hydrolase type, mention may be made in particular of enzymes with hydrolytic activity toward biopolymers.

Among these enzymes that are capable of hydrolyzing biopolymers, mention may be made in particular of glycoside hydrolases, which include glycosidases.

The term "glycoside hydrolases" includes, inter alia, xylanases, cellulases, chitinases, pectinases, mannases and Cellulyve (registered trademark).

Among the biopolymer-hydrolyzing enzymes, examples that may be mentioned include proteases, esterases, nucleases and ligninases.

The polymer or the mixture of polymers studied in the process of the invention is preferably present in the micro-deposits in a content of between 99.5% to 95% by weight relative to the total weight of the layer of said deposits in which it is present.

Preferably, the polymer studied in the process of the invention is preferably present in the micro-deposits in a content of between 99.5% to 95% by weight relative to the total weight of said deposits.

The polymer(s), preferably the polymer, may be chosen from biopolymers.

Such biopolymers may be in an isolated form (i.e. distinct polymer chains), in aggregated form (i.e. entangled polymer chains) or in crystalline form (i.e. polymer chains organized in an ordered repeating pattern).

The polymer(s) may be biopolymers, notably chosen from the group consisting of oligosaccharides and polysaccharides such as cellulose, xylan, pectin, chitosan, chitin, xyloglucan, beta-glucan, and arabinoxylan; peptides and proteins such as bovine or human serum albumin and glutenin; nucleic acids such as deoxyribonucleic acids and ribonucleic acids; cutin, suberin and lignin.

Preferably, the polymer is a biopolymer, notably chosen from the group consisting of oligosaccharides and polysaccharides such as cellulose, xylan, pectin, chitosan, chitin, xyloglucan and arabinoxylan; peptides and proteins such as bovine or human serum albumin and glutenin; nucleic acids such as deoxyribonucleic acids and ribonucleic acids; cutin, suberin and lignin.

The mixture of polymers may include a biopolymer, notably chosen from the group consisting of oligosaccharides and polysaccharides such as cellulose, xylan, pectin, chitosan, chitin, xyloglucan, beta-glucan and arabinoxylan; peptides and proteins such as bovine or human serum albumin and glutenin; nucleic acids such as deoxyribonucleic acids and ribonucleic acids; cutin, suberin and lignin.

The polymer(s), preferably the polymer, is advantageously immobilized on the support.

This immobilization may be generated by bonds (i) of covalent or "chemical" type (crosslinking) and/or (ii) of noncovalent or "physical" type (electrostatic, hydrogen, Van der Waals force).

In case (i) above, the micro-deposits contain, for example, a resin present in a content of between 0.5% to 5% by weight relative to the total weight of the micro-deposits, this resin preferably being a thermosetting resin, for example melamine formaldehyde.

For the choice and implementation of such a resin, reference may be made to the following documents: Ducere et al. Sensors and Actuators B: Chemical 2005, 106(1), 331-334, Wu et al. Separation and Purification Technology 2009, 68(1), 97-104, and Schuler et al. Biomacromolecules 2001, 2(3), 921-926.

For example, crosslinking with melamine-urea-formaldehyde or melamine-formaldehyde resins (also referred to as "MUF" or "MF") has the following advantages:
the crosslinking reaction may take place with numerous chemical functions (alcohol, amine, phenol), thus making it possible to crosslink a large number of classes of biopolymers;
water-soluble resin formulations exist;
crosslinking is simple: the monomer is stable at room temperature and it reacts when the film is brought to 90° C. under a dry atmosphere for one hour, this treatment being compatible with the majority of biopolymers.

In the embodiment in which the compound is an enzyme, the process according to the invention makes it possible to analyze the enzymatic degradation activity of natural polymers, or mixtures of polymers, typically of biopolymers such as polysaccharides or lignins, or of synthetic polymers, in a context in which the number of enzymes to be tested is large and the cost of the test is reduced. The invention makes it possible to perform the test in the field, with the naked eye, without any special equipment.

When the interaction between the polymer and the compound brings about degradation of the polymer by the compound, the micro-deposit containing the polymer will decrease in volume. If the polymer is not sensitive to the compound with which it is placed in contact, the micro-deposit containing the polymer will substantially maintain its volume and its shape.

The decrease in volume of the micro-deposits brings about, at the macroscopic scale, a difference in appearance relative to the micro-deposits which substantially conserve their volume. This difference in contrast is observable with the naked eye.

According to an example of implementation of the invention, a comparison of the appearance of a set of micro-deposits exposed to the compound and of a set of micro-deposits not exposed to the compound is made, in order to detect a change in appearance. This comparison may be made without magnification, in reflected light.

According to one embodiment, the observation of the appearance of contrast is performed using one or more suitable measuring instruments, notably using a camera and preferably an image processing program. This program may notably automatically detect a variation in appearance and the appearance of a contrast, or even may quantify it.

According to another of its aspects, a subject of the invention is also a process for detecting the sensitivity of a polymer to a compound, including the steps consisting in:
- exposing a periodic arrangement of micro-deposits, notably of lens-shaped micro-deposits, including the polymer, to the compound,
- detecting by exposing this periodic arrangement to a suitable light, notably coherent light, a change in the spatial distribution of the intensity of the light diffracted by this network, linked to a variation in the dimensions and/or refractive index of the micro-deposits of this arrangement under the effect of an interaction between the polymer and the compound.

The invention also relates to a process for detecting the sensitivity of one or more polymers to a compound, including the steps consisting in:
- exposing a periodic arrangement of micro-deposits, notably of lens-shaped micro-deposits, including the polymer(s), to the compound,
- detecting by exposing the surface of this periodic arrangement to a suitable light, notably coherent light, a change in the spatial distribution of the intensity of the light diffracted by this network, linked to a variation in the dimensions and/or refractive index of the micro-deposits of this arrangement under the effect of an interaction between the polymer(s) and the compound.

The invention makes it possible 1) to identify the compound or the mixture of compounds which, for example, most efficiently degrades a polymer or a mixture of polymers and 2) to classify a set of compounds or a mixture of compounds relative to their kinetics, for example, of degradation of a polymer or of a mixture of polymers.

The invention makes it possible, if so desired, to go back up to the loss of volume of the solid deposits induced by the degradation due to the enzymatic reaction. It makes it possible to do so either quantitatively in the context of a laboratory using an optical system, or qualitatively in the field with the naked eye or potentially quantitatively using a portable reading instrument.

Advantages of the process according to preferred implementation variants of the invention are the following:
- possibility of studying a single compound or a cocktail of compounds,
- capacity for depositing a biopolymer/polymer or a set of polymers or mixtures of polymers of different compositions on the same support, in the same pattern or from one macro-pattern to another,
- detection of the compound-polymer interaction without using a marker,
- sensitivity level equivalent to or better than that of conventional biochemical techniques using a fluorogenic or chromogenic substrate for an equivalent incubation time,
- possibility of modulating the detection dynamics as a function of the type of sample tested (physicochemical properties of the deposit),
- integration of a twofold level of analysis: a) macroscopic making it possible to visualize with the naked eye whether or not there is hydrolysis, b) macroscopic using an instrument that is compatible with the detection system with the technologies loaded on recent cellphones making it possible to extract quantitative data regarding the activities of the compounds.

In the context of the functional diagnosis of microbial ecosystems or of isolated strains, the capacity for manufacturing a low-cost, disposable enzymatic test which rapidly gives an answer is of undeniable interest. Specifically, whether for environmental applications (degradation performance of a polluting polymer), in human health (degradation of intestinal mucus by opportunistic commensals, or pathogens), or in animal nutrition (degradation performance of dietary fibers by the digestive ecosystem or by exogenous enzyme cocktails added to the feed to increase the energy efficiency), semi-quantitative assay of the degradation activities of polymers is a necessary prerequisite for the characterization and engineering of ecosystems to optimize the services rendered (at the environmental level, or for the health of the host when it is a human or animal ecosystem).

The current use of enzymes in certain industrial sectors (textile, human and animal nutrition) requires during production that tests be performed to check the conformity of the final product, and the process according to the invention thus turns out to apply also to quality control.

A subject of the invention is also a process for detecting a change of state of a polymer under the action of a compound to which the polymer is sensitive, including the steps consisting in:
- exposing at least one lens-shaped micro-deposit, including the polymer, to conditions which bring about an at least partial change of state,
- detecting a change in the spatial distribution of the intensity of the light reflected or transmitted by this micro-deposit, linked to a variation in the dimensions and/or refractive index of this micro-deposit under the effect of this change of state.

The invention also relates to a process for detecting a change of state of one or more polymers under the action of a compound to which the polymer(s) are sensitive, including the steps consisting in:
- exposing at least one lens-shaped micro-deposit, including the polymer(s), to conditions bringing about an at least partial change of state,
- detecting, by illuminating the surface of this micro-deposit, a change in the spatial distribution of the intensity of the light reflected or transmitted by this micro-deposit, linked to a variation in the dimensions and/or refractive index of this micro-deposit under the effect of this change of state.

Device

The invention also relates to a device that is particularly suitable for performing the process according to the invention as defined above, including:
- a support,
- a plurality of individualized micro-deposits borne by the support, which are preferably lens-shaped, each micro-deposit including at least one polymer that is sensitive to a compound.

The characteristics of the invention described above in reference to the process are also valid for the device, and vice-versa.

The micro-deposits may be positioned closely enough together for the interaction effect between the polymer(s) and the compound, preferably between the polymer and the compound, to be visible to the naked eye in the form of an intensity contrast.

The device may include an optical system including, for example, a light source illuminating at a fixed angle the surface of the device and an optical sensor (camera or the like) collecting the light reflected by the micro-deposits acting as microlenses.

Assembly

A subject of the invention is also an assembly including a device according to the invention and a compound interacting with said polymer to lead to a variation in the dimensions and/or refractive index of the micro-deposits. This variation may result from an enzymatic degradation reaction between the polymer and the compound.

The invention also relates to an assembly including a device according to the invention and a compound interacting with the polymer(s) to lead to a variation in the dimensions and/or refractive index of the micro-deposits. This variation may result from an enzymatic degradation reaction between the polymer(s) and the compound.

Process for Manufacturing the Device

The invention also relates to a process for manufacturing a device according to the invention, including the deposition by printing onto the support of dots of an ink containing the polymer(s) to form the micro-deposits.

The invention also relates to a process for manufacturing a device according to the invention, including the deposition by inkjet printing onto the support of dots of an ink containing the polymer(s) to form the micro-deposits.

The invention also relates to a process for manufacturing a device according to the invention, including the deposition by printing onto the support of dots of an ink containing said polymer to form the micro-deposits.

Preferably, the printing technique is of the inkjet type.

According to a preferred embodiment, this manufacturing process comprises a step of crosslinking the ink so as to convert the ink dots into individualized solid micro-deposits.

The process may include modification of the wettability of the support prior to printing the micro-deposits, in order to adjust the thickness of the micro-deposits, notably to obtain a convex shape for same and to modify the homogeneity of the thickness.

According to a variant of the process for manufacturing the device, the deposition by printing on the support is performed in several successive spatially superposed passes, so as to obtain multilayer micro-deposits, each pass making it possible to deposit a layer of ink.

Preferably, the number of passes is equal to two. This makes it possible to form on the support micro-deposits including two superposed layers, notably with a core-shell architecture. In this case, the micro-deposit has a first layer corresponding to the core, and a second layer corresponding to the shell.

The first layer may be positioned on the support, preferably in contact therewith, and may be lens-shaped.

The second layer may at least partially and preferably totally cover the first layer and may have a shape complementary to that of the first layer.

In a first step, the first layer is deposited on the support, preferably in contact therewith, during a first pass.

In a second step, the second layer is deposited during a second pass so that said second layer at least partially and preferably totally covers the first layer.

The deposition of the second layer is preferably performed when the first layer is crosslinked.

It is thus possible, by using a different ink in the first and second layers, to obtain micro-deposits consisting of layers of different nature, for example each including a different polymer, or else different ratios of mixed polymers.

The thickness of the multilayer micro-deposits is preferably between 100 nm and 1500 nm, better still between 100 and 1000 nm, the thickness of each multilayer micro-deposit advantageously passing through a single maximum.

The largest dimension of the multilayer micro-deposits is preferably between 10 μm and 100 μm.

The thickness of the first layer of the multilayer micro-deposit is preferably between 30 nm and 1300 nm, better still between 70 nm and 800 nm.

The largest dimension of the first layer of the multilayer micro-deposit is preferably between 5 μm and 95 μm.

Aqueous Ink

A subject of the invention is also an ink, preferably an aqueous ink, which is particularly suitable for performing the process for manufacturing a device according to the invention, including:
- the polymer(s), preferably the polymer,
- a binder, preferably a resin, notably melamine-formaldehyde, and
- an organic cosolvent chosen to allow the formation of a micro-deposit of convex shape during the drying of the ink, preferably dimethyl sulfoxide (DMSO).

The invention also relates to an ink, preferably an aqueous ink, which is particularly suitable for performing the process for manufacturing a device according to the invention, including:
- the polymer(s), which are notably degradable with an enzyme, preferably chosen from oligosaccharides and polysaccharides such as cellulose, xylan, pectin, chitosan, chitin, xyloglucan, beta-glucan and arabinoxylan; peptides and proteins such as bovine or human serum albumin and glutenin; nucleic acids such as deoxyribonucleic acids and ribonucleic acids; cutin, suberin and lignin,
- a binder, preferably a resin, notably melamine formaldehyde, and
- an organic cosolvent chosen to allow the formation of a convex-shaped micro-deposit during the drying of the ink, preferably DMSO, the ink preferably being packaged in an inkjet printer cartridge.

Preferably, the polymer content in the ink is from 1 mg/mL to 10 mg/mL relative to the volume of the ink.

In the case of a mixture of polymers, the proportions of each of the polymers in the mixture are chosen as a function of the intended application.

Preferably, the resin content in the ink is between 0.01 mg/mL and 0.1 mg/mL relative to the volume of the ink.

The polymer(s)/resin ratio may be between 100 and 300.

The polymer(s)/resin ratio is preferably equal to 200.

The viscosity of the ink at 20° C. is preferably between 5 mPa·s and 20 mPa·s, preferentially equal to 15 mPa·s±3 mPa·s, notably to 17 mPa·s.

The surface tension is, for example, 62 mN·m$^{-1}$, preferably being less than or equal to 70 mN·m$^{-1}$.

The ink is preferably packaged in an inkjet printer cartridge.

The ink may comprise at least one film-forming agent, said agent allowing the easy formation of the micro-deposit.

Said film-forming agent is chosen, for example, from: polyallylamine, polyacrylamide, polyvinylpyrrolidone, and copolymers thereof.

Preferentially, said film-forming agent is poly(allylamine) hydrochloride PAH.

The content of film-forming agent in the ink is preferentially between 0% and 10% by volume.

The ink may comprise at least one catalytic agent, this agent making it possible to facilitate the crosslinking of the micro-deposit.

Said catalytic agent may be chosen as a function of its influence on the annealing temperature required for the formation of the micro-deposit.

Said catalytic agent is chosen, for example, from acids.

Preferentially, said catalytic agent is hydrochloric acid.

The content of catalytic agent in the ink is preferentially between 0% and 10% by volume.

The ink is preferably free of pigments and dyes.

The presence of the organic cosolvent is useful for avoiding the "coffee stain" effect during the drying of the ink, leading to the formation of a deposit of less uniform thickness on the support. Solvents other than DMSO may be used, for example ethylene glycol or N,N-dimethylformamide (DMF), inter alia.

FIG. 1 shows an example of a device 1 according to the invention, including a support 10 which is, for example, a silicon wafer that has been made hydrophobic, on which are formed macro-patterns 20 in the form, for example, of squares placed with respective spacings $D_X$ and $D_Y$ in directions X and Y, corresponding to those of the wells of a conventional well plate.

The side D of a macro-pattern 20 measures, for example, between 3 and 5 millimeters and the values $D_X$ and $D_Y$ are, for example, between 3 and 5 mm also.

Each macro-pattern 20 which has a millimetric size is formed from a raster of micro-deposits 21, these micro-deposits being close enough to give with the naked eye a uniform appearance to each macro-pattern 20. For example, the separation $d_X$ in the X direction and the separation $d_Y$ in the Y direction are between 50 and 340 micrometers, or even 50 and 100 micrometers, the diameter d of a micro-deposit 21 being, for example, between 10 and 100 micrometers and its height h (which corresponds to the thickness) between 100 and 1500 nanometers.

In the example under consideration, the micro-deposits 21 are deposited by inkjet printing with a uniform spacing. The ink has a formulation that is suited to the formation of a convex outer surface.

Preferably, the micro-deposits 21 allow, due to the difference in refractive index with the support 10, and also to the reflective nature of the support 10, the formation of interference fringes such as Newton rings. These interference patterns may be observed by microscope by illuminating the device 1 with white light.

Figure 10:
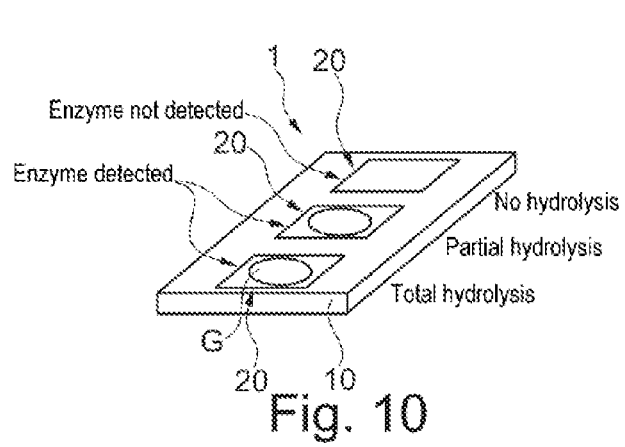
FIG. 10 illustrates the effect of the enzymatic degradation on microlenses, FIG. 11 also illustrates the effect of the enzymatic degradation on microlenses.
Figure 11:
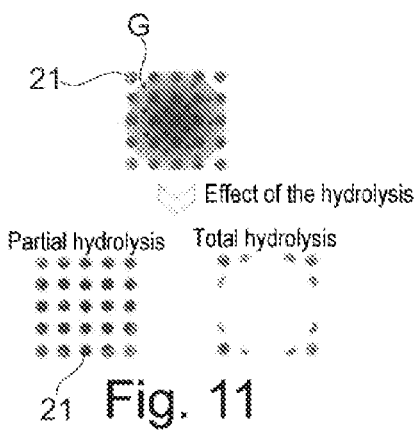

The device 1 may be used by depositing on each macro-pattern 20 a drop G of a test compound, as illustrated in FIGS. 10 and 11. Depending on whether or not a degradation reaction of the polymer by hydrolysis takes place, the change in appearance of the macro-pattern 20 may be observed with the naked eye.

FIG. 11 shows at the top in the center the situation in which there is no reaction between the enzyme and the polymer, the hydrolysis reaction being zero, and at the bottom on the left the case where the hydrolysis is partial, or even total at the bottom on the right, which allows detection of the enzyme.

This qualitative approach may be completed by a quantitative approach by examination using an optical system which makes it possible to visualize the degradation activity of one or more chemical products on the polymer deposits.

This system is composed, for example, of a light source illuminating at a fixed angle the surface of the device and of an optical sensor (camera or the like) collecting the light reflected by the micro-deposits acting as microlenses.

Figure 5:
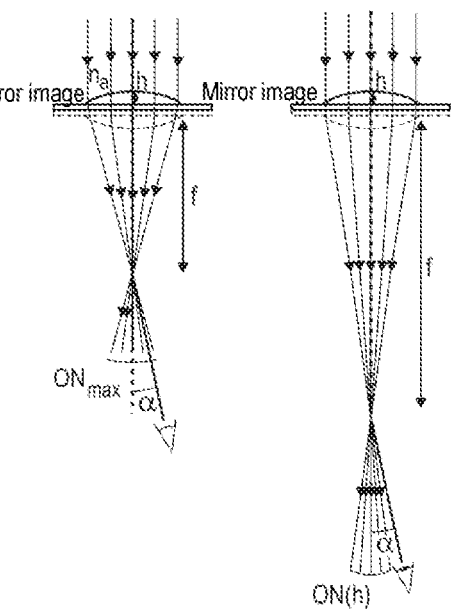
FIG. 5 illustrates the effect of the degradation on the focal distance.

The sensor makes it possible to extract quantitative data regarding the rate of degradation of the deposits by means of the impact of the degradation on the optical response of the microlenses. Simple reading of the visible light intensity in the degraded patterns is then sufficient to quantify the loss of material. Specifically, during the degradation of the lenses, as illustrated in FIGS. 4 and 5, their reduction in diameter and in thickness changes their focal distance and consequently their numerical aperture. Thus, the change in the amount of light received at a given angle is a function of this degradation.

FIGS. 6A to 6D show images of microlenses according to the invention, illuminated with a four-LED light source.

Figures 6A, 6B, 6C, 6D:
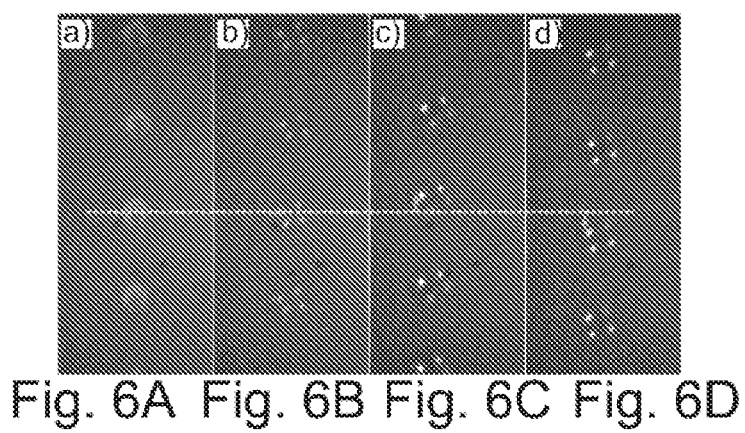
FIGS. 6A, 6B, 6C, and 6D represent images obtained by observation with a light microscope of the microlenses.

FIG. 6A corresponds to a development on the support, showing the position of the micro-deposits.

FIG. 6B corresponds to a development at ±100 μm of the surface, revealing the formation of an image of the source.

FIGS. 6C and 6D illustrate the movement of the image of the source during the lateral movement of the light source, confirming the lens effect.

Figure 8:
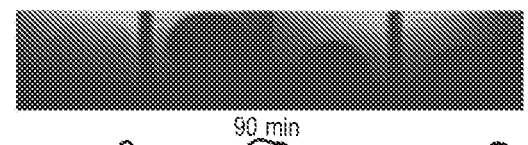
FIG. 8 is an extract of an acquisition film by translation of the microlens profiles, acquired at an angle of 2° relative to the specular reflection.

For the acquisition of the rates of degradation of the polymer of the microlenses, two methods are possible:

at a fixed angle: the light source and the camera are positioned statically on either side of the substrate and said substrate travels in a translation motion. For each pattern, the intensity profile produced by the degradation thereof by the enzyme is extracted. Examples of intensity profiles are given in FIG. 8, acquired at an angle of 2° relative to the specular reflection.

Figure 7:
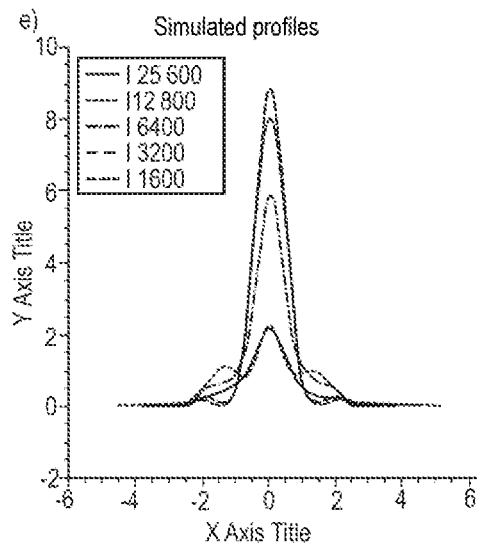
FIG. 7 is a simulation result revealing the link between the degradation and the intensity at a fixed angle of observation.
Figure 13:
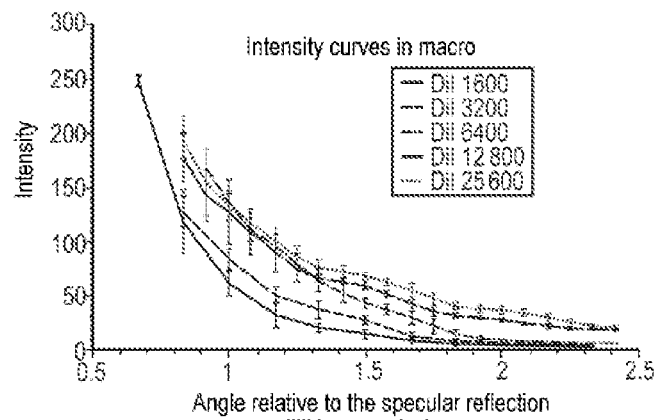
FIG. 13 illustrates the intensity of the reflection of the micro-deposits at different angles for different dilutions of the enzymatic solution.

FIG. 7 gives a simulation result showing the relationship between the degradation and the intensity at a fixed angle.

at a variable angle: the position of interest is illuminated with a source and the camera rotates about the sample on an axis. FIG. 13 gives the intensity of the reflection at different angles for different dilutions of enzymatic solution.

By extracting the data obtained by the second method at a specific angle, a set of data equivalent to the first method is obtained.

EXAMPLES

Example 1

First Step: Preparation of the Ink

A first aqueous ink formulation suitable for inkjet printing was prepared according to the specificities below, in which the polymer used is arabinoxylan:

| Mono-polymer ink (formulation 1) | Variant 1 | Variant 2 |
|---|---|---|
| Arabinoxylan Megazyme-wheat Arabinoxylan - Medium viscosity 22 cSt - 323 Kd molecular weight | 5 mg/mL | 3 mg/mL |
| Melamine formaldehyde (resin) ®Resimene AQ-7551 sold by INEOS Melamines | 0.025 mg/mL | 0.015 mg/mL |
| DMSO CAS 67-68-5 | 10% vol | 10% vol |
| Poly(allylamine) hydrochloride PAH sold by Polyscience, Mw-120000-200000 g/mol | 0.004 mg/mL | 0.004 mg/mL |
| Hydrochloric acid HCl | 0.01 mM | 0.01 mM |

The viscosity of the ink obtained according to variant 1 of formulation 1 is 15 mPa·s (at the ejection temperature of 20-30° C.) and the surface tension is of the order of 50 Nm (at the ejection temperature).

In the case of variant 1 of formulation 1, the polymer/resin ratio is 200 (5/0.025).

In the case of variant 2 of formulation 1, the polymer/resin ratio is also 200 (3/0.015).

Below, a second formulation in which the polymer used is beta-glucan, and a third formulation in which the polymers used are arabinoxylan and beta-glucan (ink with a 50%/50% mixture of polymers), are proposed as illustration of the invention:

| Mono-polymer ink (formulation 2) | Variant 1 | Variant 2 |
|---|---|---|
| Beta-glucan | 7 mg/mL | 3 mg/mL |
| Melamine formaldehyde (resin) ®Resimene AQ-7551 sold by INEOS Melamines | 0.025 mg/mL | 0.015 mg/mL |
| DMSO CAS 67-68-5 | 10% vol | 10% vol |
| Poly(allylamine) hydrochloride PAH sold by Polyscience, Mw-120000-200000 g/mol | 0.004 mg/mL | 0.004 mg/mL |
| Hydrochloric acid HCl | 0.01 mM | 0.01 mM |

In the case of variant 1 of formulation 2, the polymer/resin ratio is 280 (7/0.025).

In the case of variant 2 of formulation 2, the polymer/resin ratio is also 200 (3/0.015).

| Multi-polymer ink (formulation 3) | Variant 1 | Variant 2 |
|---|---|---|
| Arabinoxylan Megazyme-wheat Arabinoxylan - Medium viscosity 22 cSt - 323 Kd molecular weight | 2.5 mg/mL | 1.5 mg/mL |
| Beta-glucan | 2.5 mg/mL | 1.5 mg/mL |
| Melamine formaldehyde (resin) ®Resimene AQ-7551 sold by INEOS Melamines | 0.025 mg/mL | 0.015 mg/mL |
| DMSO CAS 67-68-5 | 10% vol | 10% vol |
| Poly(allylamine) hydrochloride PAH sold by Polyscience, Mw-120000-200000 g/mol | 0.004 mg/mL | 0.004 mg/mL |
| Hydrochloric acid HCl | 0.01 mM | 0.01 mM |

In the case of variant 1 of formulation 3, the polymer/resin ratio is 200 ((2.5+2.5)/0.025).

In the case of variant 2 of formulation 3, the polymer/resin ratio is also 200 ((1.5+1.5)/0.015).

Second Step: Modification of the Support

A silicon wafer is used as support.

In order to obtain convex-shaped deposits and to avoid spreading of the droplets, the upper face of the wafer is treated with $C_4F_8$ to be made hydrophobic.

Third step: Inkjet printing

The ink prepared beforehand according to variant 1 of formulation 1 was loaded into an inkjet printer and ink dots are printed on the support, as raster dots.

The printing parameters are:
ink ejection temperature: room temperature (20° C.-30° C.),
ejection volume of the droplets (per micro-deposit): 65 μL±5 μL,
micro-deposit thickness: less than 1 μm,
ejection speed of the droplets: 5 to 6 m/s, and
macro-pattern: square matrix with a side length of 4 cm with spacing between two micro-deposits in the macro-pattern equal to 70 μm Fourth Step: Thermal Crosslinking of the Ink Deposits The support onto which the liquid ink dots were deposited is placed at 130° C. for 10 to 180 minutes until crosslinking of the resin and solidification of the micro-deposits are complete.

Use of the Detection Device

The device thus manufactured was used to study the kinetics of degradation of the polymer present in the deposits, namely arabinoxylan, by enzymatic solutions of commercial xylanase each having a different level of activity.

First, the device was immersed in water at 37° C. for 2 hours, and then immersed in an aqueous solution of BSA (bovine serum albumin) at 0.25 g/L at 37° C. for 1 hour, in order to passivate the surface between the polymer deposits, which improves the measurement sensitivity.

In this example, the protein used as passivation agent is BSA. However, the invention is not limited to this particular case.

For example, proteins other than BSA may be used as passivation agent, such as ovalbumin or lysozyme.

The concentration range of passivation agent in the bath in which the device is immersed is preferentially between 0.1 g/L and 1 g/L.

Xylanase solutions of different concentration were prepared, having enzymatic activities ranging from 0.23 nkat/mL (dilution to 102 400—test No. 2) up to 14.8 nkat/mL (dilution to 1600—test No. 8).

A drop of 7 μL of each of these solutions is deposited on a corresponding macro-pattern. As control, a drop of acetate buffer is deposited on another pattern.

After incubation for 60 minutes at room temperature, rinsing with water and drying of the device, different results for each concentration were observed with the naked eye (cf. table below).

| Test No. | Enzymatic activity (nkat/mL) | Dilution factor (relative to the commercial xylanase solution) | Result observed (with the naked eye) |
|---|---|---|---|
| 1 (control) | 0 | — | — |
| 2 | 0.23 | 102 400 | — |
| 3 | 0.46 | 51 200 | — |
| 4 | 0.92 | 25 600 | + |
| 5 | 1.85 | 12 800 | ++ |
| 6 | 3.7 | 6400 | +++ |
| 7 | 7.4 | 3200 | +++ |
| 8 | 14.8 | 1600 | +++ |

This test made it possible to estimate a sensitivity threshold approximately located at 0.92 nkat/mL (i.e. $6.4 \times 10^{-3}$ nkat).

Figure 9:
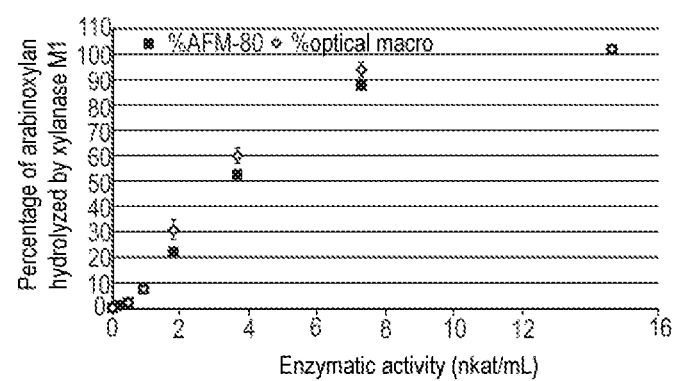
FIG. 9 represents a comparison between the Volume of the microlenses measured b ATM and that measured the process according to the invention.

FIG. 9 shows the good correlation between the measurements of the volume of the microlenses taken by AFM and the measurements according to the invention.

Example 2

Figure 12:
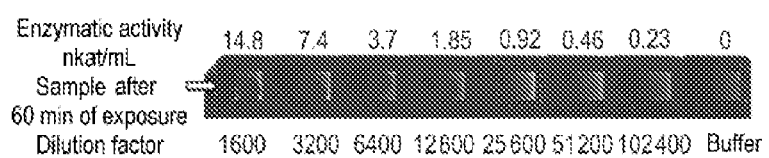
FIG. 12 is a comparison of the enzymatic activity at various degrees of dilution, obtained using a device according to the invention.

FIG. 12 represents a photograph of an assembly of macro-patterns according to the invention which has been placed in contact with different concentrations of xylanase (14.8 0.23 nkat/mL) for 60 minutes after hydration by immersion in water for 2 hours at 37° C. followed by passivation for 1 hour in a solution of BSA at 0.25 g/L at 37° C.

This photograph reveals the detection limit with the naked eye for a dilution factor of 25 600.

The invention claimed is:

1. A process for detecting sensitivity of one or more polymers and/or of one or more mixtures of polymers to a compound, comprising:
   exposing at least one lens-shaped micro-deposit, including the polymer(s) and/or the mixture(s) of polymers, to the compound,
   detecting, by illuminating the surface of the micro-deposit, a change in the spatial distribution of the intensity of the light reflected or transmitted by the micro-deposit, linked to a variation in the dimensions and/or refractive index of the micro-deposit, under the effect of an interaction between the polymer(s) and/or the mixture(s) of polymers and the compound;

wherein the micro-deposits are arranged in a periodic network and illuminated with coherent light, and the spatial distribution of the light is detected in a diffraction pattern produced by the network.

2. The process as claimed in claim 1, wherein several micro-deposits are exposed to the compound and the detection of the change in spatial distribution of the light intensity is performed by observing said micro-deposits.

3. The process as claimed in claim 1, wherein the micro-deposit(s) are illuminated with a point or linear source.

4. The process as claimed in claim 1, wherein the detection of the change in the spatial distribution of the light intensity is performed in the region of the specular reflection.

5. The process as claimed in claim 1, wherein the detection of the change in the spatial distribution of the light intensity is performed with a matrix sensor.

6. The process as claimed in claim 1, wherein information regarding the variation in the dimension of the micro-deposit is generated from the change observed, by comparison with reference data.

7. The process as claimed in claim 1, wherein thickness of the micro-deposits range between 100 and 5000 nm.

8. The process as claimed in claim 1, wherein largest dimension of the micro-deposits range between 10 and 100 microns.

9. The process as claimed in claim 1, wherein thickness of each micro-deposit passes through a single maximum.

10. The process as claimed in claim 1, wherein each micro-deposit has a convex outer surface.

11. The process as claimed in claim 1, wherein the detection of the change in the spatial distribution is observed without magnification.

12. The process as claimed in claim 1, wherein the micro-deposits are arranged in the form of raster dots.

13. The process as claimed in claim 1, wherein the micro-deposits are arranged in a periodic network and illuminated with coherent light, and the spatial distribution of the light is detected in a diffraction pattern produced by the network, in order to measure degradation of the polymer(s).

14. The process as claimed claim 1, wherein the micro-deposits are arranged in macro-patterns separated from each other.

15. The process as claimed in claim 1, wherein the micro-deposits are located on a reflective support.

16. The process as claimed in claim 1, wherein the micro-deposits are located on a hydrophobic support.

17. The process as claimed in claim 1, wherein the compound is an enzyme.

18. The process as claimed in claim 1, wherein the polymer(s) are biopolymers.

19. A device for performing the process as claimed in claim 1, comprising:
a support,
a plurality of individualized solid lens-shaped micro-deposits borne by the support, each micro-deposit including comprising at least one polymer that is sensitive to a compound.

20. The device as claimed in claim 19, wherein a largest dimension of the micro-deposits are between 10 and 100 microns.

21. The device as claimed in claim 19, wherein the thickness of each micro-deposit passes through a single maximum.

22. The device as claimed in claim 19, wherein each micro-deposit has a convex outer surface.

23. The device as claimed in claim 19, wherein the micro-deposits are arranged in the form of raster dots.

24. The device as claimed in claim 19, wherein the micro-deposits are arranged in macro-patterns separated from each other.

25. The device as claimed in claim 19, wherein the micro-deposits are positioned closely enough so that the interaction effect between the polymer(s) and the compound is visible to the naked eye in the form of an intensity contrast.

26. The device as claimed in claim 19, wherein the support is reflective.

27. The device as claimed in claim 19, wherein the support is hydrophobic.

28. An assembly including a device as defined in claim 19 and a compound interacting with the polymer(s) to lead to a variation in the dimensions and/or refractive index of said micro-deposit.

29. A process for manufacturing a device as defined in claim 19, comprising the deposition by printing onto the support of dots of an ink containing the polymer(s) to form the micro-deposits.

30. A process for detecting a change of state of one or more polymers under the action of a compound to which the polymer(s) are sensitive, comprising:
exposing at least one lens-shaped micro-deposit, comprising the polymer(s), to conditions causing at least a partial change of state of the polymer(s),
detecting, by illuminating the surface of the micro-deposit, a change in the spatial distribution of the intensity of the light reflected or transmitted by the micro-deposit, linked to a variation in the dimensions and/or refractive index of the micro-deposit resulting from said change of state;
wherein the micro-deposits are arranged in a periodic network and illuminated with coherent light, and the spatial distribution of the light is detected in a diffraction pattern produced by the network.

31. A process for detecting the sensitivity of one or more polymers to a compound, comprising:
exposing a periodic network of lens-shaped micro-deposits comprising the polymer(s), to the compound,
detecting, by exposing the surface of the periodic network to a suitable light, a change in the spatial distribution of the intensity of the light diffracted by the network, linked to a variation in the dimensions and/or refractive index of the micro-deposits of the periodic network resulting from the effect of an interaction between the polymer(s) and the compound;
wherein the micro-deposits are illuminated with coherent light, and the spatial distribution of the light is detected in a diffraction pattern produced by the periodic network.

* * * * *